US00PP12487P2

(12) United States Plant Patent
Trees

(10) Patent No.: US PP12,487 P2
(45) Date of Patent: Mar. 26, 2002

(54) GERANIUM PLANT NAMED 'BALCOLDEPI'

(75) Inventor: Scott C. Trees, Shell Beach, CA (US)

(73) Assignee: Ball FloraPlant, A Division of Ball Horticultural Co., West Chicago, IL (US)

( * ) Notice: Subject to any disclaimer, the term of this patent is extended or adjusted under 35 U.S.C. 154(b) by 0 days.

(21) Appl. No.: 09/821,995

(22) Filed: Mar. 31, 2001

(51) Int. Cl.[7] ..... A01H 5/00

(52) U.S. Cl. ..... Plt./332

(58) Field of Search ..... Plt./332

*Primary Examiner*—Bruce R. Campell
*Assistant Examiner*—Kent L. Bell
(74) *Attorney, Agent, or Firm*—C. A. Whealy

(57) ABSTRACT

A new and distinct cultivar of Geranium plant named 'Balcoldepi', characterized by its upright and mounded growth habit; freely basal branching habit; medium green leaves with dark brown zonation pattern; dark pink-colored double flowers; and numerous flower umbels per plant.

1 Drawing Sheet

BACKGROUND OF THE INVENTION

The present invention relates to a new and distinct cultivar of Geranium plant, botanically known as *Pelargonium peltatum*, and hereinafter referred to by the name 'Balcoldepi'.

The new Geranium is a product of a planned breeding program conducted by the Inventor in Arroyo Grande, Calif. The objective of the breeding program was to develop new cultivars with freely-branching and vigorous growth habit, medium or dark green-colored foliage, uniform flowering, and interesting flower and foliage colors.

The new Geranium originated from a cross made by the Inventor of the proprietary *Pelargonium peltatum* selection 8295-42 as the female, or seed, parent with the proprietary *Pelargonium peltatum* selection 8315-B as the male, or pollen, parent. The cultivar 'Balcoldepi' was discovered and selected by the Inventor as a flowering plant within the progeny from this cross in a controlled environment in Arroyo Grande, Calif., in 1998.

Asexual reproduction of the new cultivar by terminal cuttings taken at Arroyo Grande, Calif., has shown that the unique features of this new Geranium are stable and reproduced true to type in successive generations of asexual reproduction.

SUMMARY OF THE INVENTION

The following traits have been repeatedly observed and are determined to be the unique characteristics of 'Balcoldepi'. These characteristics in combination distinguish 'Balcoldepi' as a new and distinct cultivar:

1. Upright and mounded growth habit.
2. Freely basal branching habit.
3. Medium green leaves with dark brown zonation pattern.
4. Dark pink-colored double flowers.
5. Freely flowering with numerous flower umbels per plant.

Plants of the new Geranium differ primarily from plants of the parent selections in flower form as flowers of the parent selections are semi-double and flowers of the new Geranium are double.

The new Geranium can be compared to the cultivar, 'Nicole', disclosed in U.S. Plant Pat. No. 7,358. However, in side-by-side comparisons conducted in Arroyo Grande, Calif., plants of the new Geranium differ from plants of the cultivar 'Nicole' in the following characteristics:

1. Plants of the new Geranium are much more freely branching and more vigorous than plants of the cultivar 'Nicole'.
2. Plants of the new geranium have longer lateral branches and longer internodes than plants of the cultivar 'Nicole'.
3. Plants of the new Geranium have larger leaves and more leaves per lateral branch than plants of the cultivar 'Nicole'.
4. Plants of the new Geranium have more flower umbels than plants of the cultivar 'Nicole'.
5. Flower color of the new Geranium is darker pink than flower color of the cultivar 'Nicole'.

BRIEF DESCRIPTION OF THE PHOTOGRAPH

The accompanying colored photograph illustrates the overall appearance of the new cultivar, showing the colors as true as it is reasonably possible to obtain in colored reproductions of this type. The photograph comprises a side perspective view of a typical flowering plant of 'Balcoldepi'. Flower and foliage colors in the photograph may differ slightly from the color values cited in the detailed botanical description which accurately describe the colors of the new Geranium.

DETAILED BOTANICAL DESCRIPTION

The cultivar 'Balcoldepi' has not been observed under all possible environmental conditions. The phenotype may vary somewhat with variations in environment such as temperature and light intensity, without, however, any variance in genotype. The following observations, measurements and comparison describe plants grown 10-cm pots in West Chicago, Ill., under commercial practice in a polycarbonate-covered greenhouse with day temperatures about 20 to 22° C., night temperatures about 18 to 20° C. and light levels about 2,500 to 3,000 foot-candles. Plants used for the photograph and description were about 8 to 10 weeks from planting rooted cuttings. In the following description, color references are made to The Royal Horticultural Society Colour Chart except where general terms of ordinary dictionary significance are used.

Botanical classification: *Pelargonium peltatum* cultivar 'Balcoldepi'.

Parentage:

*Female parent.*—Proprietary *Pelargonium peltatum* selection 8295-42.

*Male parent.*—Proprietary *Pelargonium peltatum* selection 8315-B.

Propagation:

*Type cutting.*—Terminal cuttings.

*Time to initiate roots.*—About 7 days at 18° C.

*Time to develop roots.*—About 21 days at 18° C.

*Root description.*—Fibrous, freely branching.

Plant description:

*General appearance.*—Upright and mounded growth habit, eventually somewhat trailing. Appropriate for 10-cm and larger containers.

*Crop time.*—Starting with a rooted cutting, about 8 to 10 weeks are required to produced a finished flowering plant in 10-cm container.

*Growth and branching habit.*—Vigorous and freely basal branching with about 12 lateral branches at the base. Pinching, that is, removal of terminal apices, is typically not required.

*Plant height* (*to top of foliage*).—About 23 cm.

*Plant width.*—About 30 cm.

*Lateral branches.*—Length: About 28 cm. Internode length: About 7.7 cm. Color: Between 146B and 147B.

*Foliage description.*—Leaves simple, generally symmetrical, abundant, opposite. Quantity of leaves per lateral branch: About 16. Length: About 4.4 cm. Width: About 8.1 cm. Shape: Reniform. Apex: Acute. Base: Cordate. Margin: Palmatifid; entire. Venation: Palmate. Texture: Smooth; slightly pubescent along veins of both surfaces, denser on lower surface. Color: Young and fully expanded foliage, upper surface: 137A; zonation pattern, 200A in color, about 3 cm in width, and located at center of leaf. Young and fully expanded foliage, lower surface: 137C. Venation, upper and lower surfaces: 146B. Petiole: Length: About 5 cm. Diameter: About 2 mm. Color: Between 146B and 147B.

Flower description:

*Flower arrangement and type.*—Dark pink-colored flowers arranged in hemispherical umbels arising from apical leaf axils. Umbels displayed above the foliage. At full flowering, usually about 13 open umbels and about 15 developing umbels per plant. Flowers double and rounded in shape. Umbels persistent. Flowers not fragrant.

*Flowering season.*—Year-round under greenhouse conditions. In the garden, flowering is continuous from spring until fall.

*Umbels.*—Number of flowers per umbel: About 8. Diameter: About 8.4 cm. Height: About 5 cm. Flower diameter: About 5.2 cm.

*Flower buds.*—Length: About 1.4 cm. Diameter: About 7 mm. Shape: Ovoid. Color: Before showing color, between 143A and 146A; when showing color, 51A.

*Petals/petaloids.*—Quantity: About 10 petals and about 4 to 8 petaloids per flower. Petaloids variable in size and shape. Arrangement: Imbricate. Petal length: Upper petals: About 3 cm. Lower petals: About 2.7 cm. Petal width: Upper petals: About 1.7 cm. Lower petals: About 1.8 cm. Petal shape: Obovate. Petal/petaloid apex: Rounded. Petal/petaloid base: Attenuate. Petal/petaloid margin: Entire. Petal/petaloid texture: Smooth. Petal/petaloid color: Upper surface: Closest to 57A with dark red, 46A, spot towards petal base; venation on upper petals, 59C. Lower surface: Closest to 52C; venation on upper petals, 59D.

*Sepals.*—Quantity: About 5, not imbricate. Length: About 1.5 cm. Width: About 4 mm. Shape: Ensiform. Apex: Narrowly acute. Margin: Entire. Texture: Pubescent. Color, upper and lower surfaces: Between 143A and 146A.

*Peduncle* (*umbel stem*).—Length: About 14.4 cm. Angle: Erect. Strength: Strong. Texture: Pubescent. Color: 146A.

*Pedicel* (*individual flower stem*).—Length: About 2.2 cm. Angle: Erect. Strength: Strong. Texture: Pubescent. Color: Between 144A and 146A overlain with slight reddish purple anthocyanin.

*Reproductive organs.*—Androecium: Anther quantity: About 10. Anther length: About 2 mm. Anther color: Closest to 86B. Pollen amount: Moderate. Pollen color: Closest to 168B. Gynoecium: Pistil quantity: One. Pistil length: About 1.5 cm. Stigma shape: Five-parted, star-shaped. Stigma color: Closest to 53B. Style length: About 4 mm. Style color: Closest to 49D.

*Seed.*—Not observed.

Disease resistance: Resistance to pathogens common to Pelargonium has not been observed.

It is claimed:

1. A new and distinct cultivar of Geranium plant named 'Balcoldepi', as herein illustrated and described.

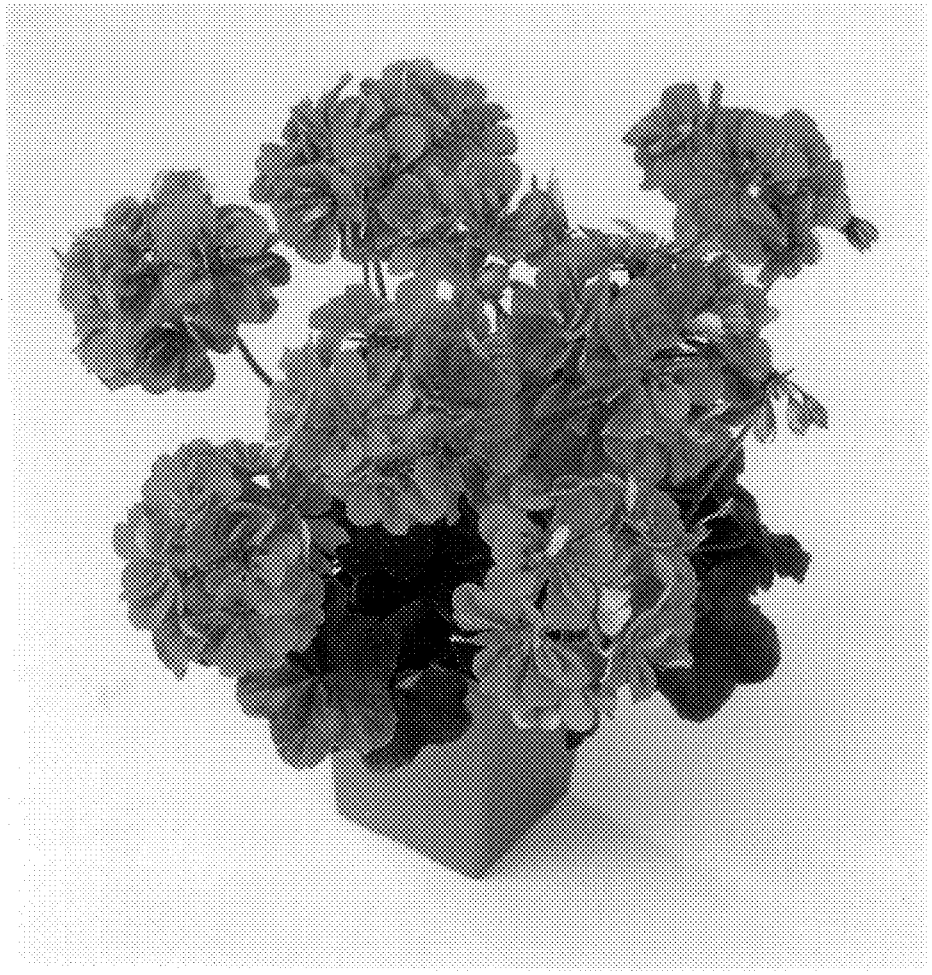

* * * * *